United States Patent [19]

Lantero, Jr.

[11] Patent Number: 4,760,024

[45] Date of Patent: Jul. 26, 1988

[54] IMMOBILIZATION OF ENZYMES

[75] Inventor: Oreste J. Lantero, Jr., Goshen, Ind.

[73] Assignee: Miles Inc., Elkhart, Ind.

[21] Appl. No.: 821,114

[22] Filed: Jan. 17, 1986

Related U.S. Application Data

[63] Continuation of Ser. No. 521,914, Aug. 10, 1983, abandoned.

[51] Int. Cl.$^4$ .................. C12N 11/10; C12N 11/02; C12P 19/24; C12P 19/12
[52] U.S. Cl. .................................. 435/178; 435/94; 435/100; 435/177
[58] Field of Search ................ 435/174–182, 435/94, 100

[56] References Cited

U.S. PATENT DOCUMENTS

| 4,089,746 | 5/1978 | Masri et al. | 435/178 |
|---|---|---|---|
| 4,094,743 | 6/1978 | Leuba | 435/178 |
| 4,167,447 | 9/1979 | Masri et al. | 435/178 |
| 4,283,496 | 8/1981 | Lee | 435/253 |
| 4,288,552 | 9/1981 | Gestrelius | 435/174 |
| 4,355,105 | 10/1982 | Lantero | 435/94 |
| 4,543,332 | 9/1985 | Jao et al. | 435/180 |

FOREIGN PATENT DOCUMENTS

| 90276 | 10/1983 | European Pat. Off. | 435/174 |
|---|---|---|---|
| 2137042 | 7/1971 | Fed. Rep. of Germany . | |
| 128474 | 11/1977 | Japan . | |

OTHER PUBLICATIONS

Muzzarelli, *Enzyme Microb. Technol.*, 1980, vol. 2, Jul. 1977.

*Primary Examiner*—David M. Naff
*Attorney, Agent, or Firm*—Jerome L. Jeffers

[57] ABSTRACT

An enzyme producing microorganism or an enzyme produced thereby is immobilized by contacting the microorganism or enzyme with polyethylenimine and adding chitosan and glutaraldehyde to form a reaction product. In a preferred embodiment, the reaction product is extruded onto the revolving plate of a spheronizing device to form spherical enzyme aggregates having enhanced physical and biocatalytic properties.

19 Claims, No Drawings

IMMOBILIZATION OF ENZYMES

This is a continuation, of application Ser. No. 521,914, filed Aug. 10, 1983, now abandoned.

BACKGROUND OF THE INVENTION

The use of enzymes derived from microbial cells to effect specific chemical transformations is well-known. In carrying out such transformations, the cell-free enzyme preparation, ruptured cells or whole cells can be efficiently used as the source of biocatalyst. The free enzymes or cells can be efficiently used in batch-type processes but do not lend themselves to continuous industrial scale operations. For example, in the conversion of glucose to fructose catalyzed by glucose isomerase or the conversion of sucrose to palatinose catalyzed by sucrose mutase, economically competitive processing requires that the substrate solution (glucose or sucrose) be passed over and through a fixed bed of the biocatalyst with continuous recovery of the product of the conversion. This processing technique has led to increased interest in the preparation of various forms of immobilized biocatalysts.

For example, Gestrelius discloses in U.S. Pat. No. 4,288,552 the use of polyethylenimine and glutaraldehyde for the immobilization of glutaraldehyde sensitive enzymes. An improvement to this method is disclosed in U.S. Pat. No. 4,355,105 wherein intracellular enzymes not sensitive to glutaraldehyde are immobilized by first being contacted with glutaraldehyde and then introducing polyethylenimine to the reaction medium. In U.S. Pat. No. 4,167,447 there is disclosed a method for the immobilization of enzymes which involves mixing an aqueous solution of an enzyme with chitosan dissolved in water at pH 3–7 to form a product which can be precipitated by the addition of an alkali or a source of sulfate ions. In another embodiment of the process disclosed in this patent, solid chitosan is cross-linked with a polyfunctional cross-linking agent such as a dialdehyde and then contacted with an aqueous solution of an enzyme. Muzzarelli discloses the immobilization of enzymes, including glucose isomerase, on chitin and chitosan in *Enzyme Microb. Technol.*, 1980, Vol. 2, July 1977. In Japanese Kokai Pat. No. Sho 51 [1976]-128, 474 a glucose isomerase immobilization method which involves the blending of glucose isomerase producing bacteria and chitosan with subsequent treatment with a polyaldehyde is disclosed. In U.S. Pat. No. 4,094,743 there is described a process in which an enzymatically active product insoluble in aqueous medium is prepared by treating chitosan as an inert support with a dialdehyde after which an enzyme is fixed to the support thus treated.

Co-pending U.S. application Ser. No. 467,851 (filed Feb. 24, 1983), now U.S. Pat. No. 4,543,332, claims the immobilization of biocatalysts using a polyamine flocculating agent and cross-linking agent with the subsequent spheronization of the immobilized product using a spheronizing device consisting of a milled friction plate as rotor situated in a cylinder such that the cylinder provides a stationary side wall for the plate while allowing it freedom to rotate. In German AS 21 37 042 there is described a method for the spheronization of enzyme compositions, particularly those which are useful in the detergent industry. The device used for such spheronization is similar to that described in the aforementioned '851 application.

In U.S. Pat. No. 4,283,496 there is disclosed a method for the conversion of glucose to fructose which involves the use of an enzyme produced by an organism from the species *flavobacterium arborescens*.

SUMMARY OF THE INVENTION

The present invention is a method for the immobilization of an enzyme producing microorganism or an enzyme produced thereby which method comprises forming a reaction product by the steps of:

(a) introducing to an aqueous medium containing an enzyme or a mass of bacterial cells containing an intracellular enzyme an aqueous solution of a polyethylenimine having a molecular weight of at least about 500 Daltons with primary amino group content of at least 10 weight percent of the polymer's amino groups;

(b) adding glutaraldehyde and an aqueous solution of chitosan to the aqueous medium to form a cross-linked reaction product; and (c) removing the cross-linked reaction product from the aqueous medium and drying it to provide an end product having biocatalytic activity.

DESCRIPTION OF THE INVENTION

The method of the present invention can be used for the immobilization of many intracellular enzymes such as, for example, glucose isomerase produced by *B. licheniformis*, *S. olivaceous* and *A. missouriensis* as well as the sucrose mutase produced by *P. rubrum*. This method may be used to immobilize extracellular enzymes as well. For example, upon homogenizing *F. arborescens* cells to where 40% of their glucose isomerase activity is soluble, complete immobilization of the soluble enzyme is observed.

The cells to be immobilized are typically grown in an aqueous nutrient medium and concentrated either by filtration or centrifugation to provide an aqueous medium containing about 10% (by weight) dry matter. The enzyme containing cells or the extracellular enzyme in the case of ruptured cells are flocculated by the addition of polyethylenimine, chitosan and glutaraldehyde to the aqueous medium. The polyethylenimine used should have a molecular weight of at least about 500 Daltons with the maximum molecular weight preferably being about 100,000 Daltons. The preferred molecular weight range is from about 40,000 to 60,000 Daltons. Immobilizations carried out using low molecular weight (below about 40,000 Daltons) result in cell aggregation, however, the aggregated cell mass could not be readily recovered by filtration. The actual chemistry of immobilization would be expected to be the same as that carried out using high molecular weight PEI. The physical properties of the cell aggregate appear to be somewhat different, such that the cell aggregate tends to bind off the filter paper. Another common method of recovery is centrifugation. Since the aggregated cell mass is actually in an insoluble form, the cell aggregate could be recovered by centrifugation. The packed-cell aggregate could then be extruded and shaped in the usual manner to obtain the desired immobilized enzyme particle. The primary amino groups of the polymer should be at least about 10 weight percent of the total amino group content of the polymer with the preferred amount being about 25 weight percent. The polyethylenimine is normally placed in aqueous solution, preferably at a concentration of from 1 to 10 weight percent before its addition to the enzyme containing medium. This is the case so that adequate mixing of the PEI into the cell mixture can be obtained. Typically, the amount of polyethylenimine added will be from 2 to 22 weight percent of the immobilized enzyme preparation.

A cross-linked reaction product is formed by the addition of glutaraldehyde and an aqueous solution of chitosan to the medium. These reactants can be added in any order or simultaneously. However, when maximum hardness of the immobilized enzyme particles is desired, the glutaraldehyde should be added first. In some cases, glutaraldehyde can partially deactivate the enzymes, so the chitosan would be added first when maximum activity is desired.

The term chitosan as used herein is intended to mean a polyamino polysaccharide obtained by N-deacetylation of chitin with strong alkali and heat. Chitin is a polysaccharide wherein the primary repeating unit in the molecule is 2-deoxy-2-acetylamino)-glucose. In general, about one out of every six units in chitin is not acetylated, whereas in chitosan essentially all the repeating units are not acylated. The extent of nonacetylation can be controlled by the severity of the deacetylation reaction. Chitin, which is distributed widely in nature such as in marine invertebrates, insects, fungi and yeast, is readily prepared by removing the impurities from shells of crab, shrimp, lobsters, crayfish and the like which are abundantly available from seafood processing plants. Typically, the amount of chitosan employed will be from 0.5 to 22 weight percent of the immobilized enzyme preparation with an amount of from 3.5 to 10 weight percent being preferred. The chitosan must be placed in aqueous solution before its addition to the enzyme containing medium because it is normally insoluble in water.

However, chitosan is soluble in dilute aqueous acid; i.e. formic, acetic, pyruvic, lactic, malic, citric, and inorganic acids with the exception of sulfuric acid in which there is formed an insoluble chitosan sulfate complex. To be effective in the present immobilization process, chitosan must become an integral portion of the immobilized cell complex. Therefore, chitosan is placed in aqueous solution before use. A solution containing about 0.2 to 1.0 weight percent chitosan is preferred and is prepared by adding the chitosan to a 0.5% solution of acetic acid. Heating the solution to about 60° C. helps dissolve the chitosan. After heating, the chitosan solution is filtered to remove insoluble residue.

Glutaraldehyde employed in this immobilization process is utilized to prevent local concentration areas that may inhibit the enzyme during the addition of the reagent. Glutaraldehyde is employed in an amount of from 4 to 26 weight percent of the immobilized enzyme with an amount of 7 to 15 weight percent being preferred.

The biocatalyst, polyethylenimine, chitosan and glutaraldehyde combine to form a bioactive reaction product which can be removed from the reaction medium by liquid/solid separatory techniques, dried, broken into particles and used for the intended biocatalytic conversion. However, it has been discovered that a more desirable physical form of the material can be obtained by drying the solid reaction product to form a wet cake containing from about 68 to 76 weight percent water and extruding the wet cake onto the rotating plate of a spheronizing device which comprises a milled friction plate as rotor situated in a cylinder such that the cylinder provides a stationary wall for the plate while allowing it freedom to rotate.

The filter cake is extruded through an orifice approximately the size of the desired diameter for the spheronized particles onto the spinning milled plate where it is disposed against the cylinder wall into an annular or doughnut-like shape with a gradient cross section. The extrudate is initially broken-down into short pieces, ideally equal to its diameter, by the friction force on the milled plate and also by the intergranular collision and friction of the moving mass. The characteristic disposition of the material results from the centrifugal force of the spinning of the plate and from the tangential force of the friction between the material and the milled surface. A smooth spinning surface does not allow the extrudate to roll but just to slide to the periphery of the plate. The characteristics of the movement would be different and, therefore, the final shape of the material would not be as uniform and spherical as desired with the use of a smooth plate. The spheronizer of the type described is a spheremaking machine which can quickly convert immobilized enzyme extrudates into small, compact, easily handled spheres.

The extrudate should preferably have a water content within the range set out above. Too low a moisture level will result in shattering of the particle during the spheronization process causing the generation of undersized particles. Too much moisture causes smearing and lumping problems during the spheronization process resulting in the generation of oversized particles. The spheronizing machine used in the following examples is marketed by Fuji Padal Co., Ltd., Osaka, Japan under the tradename Marumerizer Q-230. This device has a rotor which is 23 centimeters in diameter. The preferred tangential velocity for forming spheres from the extrudate used in this invention is 4.5 to 12 meters per second (tangential velocity = RPM ÷ 60 × $\pi$ × diameter of plate). Accordingly, the rotation of the 23 cm diameter plate would be from 500 to 1,000 revolutions per minute in order to achieve the desired spheronization results. If the rotation speed is too great, the plate will tend to spin the extruded enzyme aggregate against the cylinder wall which will create undesirable particles, whereas rotating the plate too slowly will not achieve the desired spheronization since there would not be provided sufficient momentum within the spinning mass for collision and friction as a down-sizing and spheronizing force. After their spheronization, the cell aggregates are dried, typically in a fluidized bed dryer.

The enzyme activity of the spheronized enzyme aggregate particles is roughly equivalent to or higher than that of ground particles indicating that the spheronization procedure is advantageous in terms of providing a particle having suitable biocatalytic activity. Aside from providing spherical particles which are inherently easier to handle than those of irregular shape, the spheres prepared by this process exhibit greater physical toughness and extended enzyme productivity in a reactor.

The method of practicing the present invention is further illustrated by the following examples:

EXAMPLE 1

A liquid culture medium consisting of 7% corn steep, 1.4% sweet whey powder and 0.15% yeast extract was adjusted to pH 8.3 whereupon 1,000 liters of the resultant were placed in a 1,500 liter fermenter. The media was sterilized for 60 minutes at 121° C., inoculated with *F. arborescens* strain ATCC 4358 and incubated at 30° C. for 18 hours. The glucose isomerase containing cells were then concentrated from the fermentation broth by centrifugation on a Westfala Model SAMR5036 centrifuge with a self-cleaning bowl. The concentrate was estimated to contain approximately 10% dry matter. Virtually no cell disruption occurred during centrifugation. The cell slurry pH was adjusted to 8.0, then heated to 70° C. and held at 70° C. for 15 minutes whereupon it was cooled to about 25° C. Little if any glucose isomerase activity was inactivated during the heat treatment. The heat treatment served two important functions: (1) it aided in the recovery of the cell material after immobilization, and (2) it inactivated a co-produced protease associated with the cells.

To 200 ml of heat-treated cell slurry, 1,000 ml of deionized (DI) water was added with stirring whereupon 40 ml of 5% (w/v) PEI (P-600 Cardova Chemical Co.) was added to the dilute cell slurry. After the PEI was thoroughly mixed into the slurry, 20 ml of 10% (w/v) glutaraldehyde (prepared from 25% commercial glutaraldehyde) was thoroughly mixed into the slurry. Then 200 ml of 0.25% (w/v) chitosan solution was added. The pH after chitosan addition was 7.8 which was adjusted to 8.0 with dilute sodium hydroxide. The pH values have ranged from 7.0 to 9.0 during this immobilization process. For this particular organism a pH of 8.0 has been chosen mainly because below pH 7.5 the flocculation process does not seem to be as pronounced as it is at pH 8.0. The chitosan solution was prepared by mixing the appropriate amount of chitosan to make a 1% solution in DI water. Then glacial acidic acid was added to a final concentration of 0.5% whereupon the mixture was heated to 60° C. while being thoroughly mixed. Practically all of the chitosan dissolved during the heating step. The hot solution was then diluted fourfold with DI water, and then filtered through Sharkskin filter paper on a Buchner funnel. The filtrate was cooled to about 25° C. and then the pH was adjusted carefully to 5.0 with 1 1N sodium hydroxide. After the chitosan addition, the slurry was left in a quiescent state for one hour. At this point, the cell mass was collected on a Buchner funnel and the cell cake extruded through a 1.0 mm die opening. After further dewatering the extruded material by drying at 60° C. it was ground into particles that passed through a 30 mesh screen but were retained on a 40 mesh screen which particles were then assayed for glucose isomerase activity and particle toughness.

The glucose isomerase activity in the particles was determined by placing a 0.1 gram of the enzyme in a 250 ml erlenmeyer flask and adding 50 ml of substrate [2M glucose, 20 mM $MgSO_4.7H_2O$, 0.5 mM $CoCl_2.6H_2O$ and 20 mM HEPES (N-2-hydroxyethylpiperazine-N'-2-ethanosulfonic acid) buffer adjusted to pH 8.0]. The dried particles were allowed to hydrate for about one hour at room temperature. At zero time, the flask was placed in a 60° C. water bath. The flask was agitated by a shaker water bath at a rate that provided particle movement. At 10 minutes and at 70 minutes, a 0.1 ml sample was removed from the assay mixture and added to 4.0 ml of 0.1M $HClO_4$. The amount of fructose formed was determined by the cysteine-$H_2SO_4$ method (Dische, Z. J. Biological Chemistry, Vol. 181, p. 379, 1949) by incubating 0.05 ml of sample with 0.5 ml of 5% cysteine and 4.5 ml of 75% $H_2SO_4$ at 37° C. for 30 minutes and reading the absorbance at 412 nm. A unit of immobilized glucose isomerase activity (IGIU) is that amount of enzyme that produces one micromole of fructose per minute.

The particle toughness was determined by measuring the work required to compress 20-40 mesh particles hydrated in 2M glucose at pH 8.0 using an Instron Universal Tester Model 1102. A full description of this method is given in co-pending U.S. application Ser. No. 467,851. The particle toughness is given in units of kg-in.

Treating 200 ml of cell slurry by the above described immobilization process resulted in 21.1 grams of dried material with an activity of 421 IGIU per gram and particle toughness of 3.9 kg-in.

EXAMPLES 2-5

Different levels of PEI were added to the heat-treated cell slurry of Example I prior to adding glutaraldehyde and chitosan. After adding the reagents for immobilization, the cell mass was collected, extruded, and dried as described in Example I. The following table (1) demonstrates the particle integrity and activity at various concentrations of PEI. Particle integrity and yield of immobilized enzyme are shown to improve with increased levels of PEI.

TABLE 1

| | Reagents (g/l of cell slurry) | | | Immobilized Enzyme | | |
|---|---|---|---|---|---|---|
| Example | PEI | GA | Chit. | Particle Toughness* (%) | Activity (IGIU/gm) | gm/l |
| 2 | 10.0 | 20.0 | 2.5 | 180 | 486 | 101 |
| 3 | 15.0 | 20.0 | 2.5 | 281 | 401 | 108 |
| 4 | 20.0 | 20.0 | 2.5 | 394 | 475 | 112 |
| 5 | 25.0 | 20.0 | 2.5 | 299 | 619 | 128 |

*Particle toughness as a percentage of Example 1 particle toughness

EXAMPLES 6-24

Different levels of glutaraldehyde were added to the cell slurry after the PEI addition as described in Example I. The influence on activity and particle integrity at two levels of PEI are illustrated by Table 2. Particle toughness is shown to increase as the glutaraldehyde level increased. The activity yield is shown to be inversely related to the glutaraldehyde level. The loss in apparent activity could result from the chemical reaction of the glutaraldehyde with the enzyme in such a manner to inactivate the enzyme or the glutaraldehyde may react with cellular components that may result in increasing the mass transport resistance of the substrate and products of the enzyme reaction. The results in Table 2 also show that more mass of immobilized enzyme was obtained at the higher levels of PEI.

TABLE 2

| | Reagents (g/l of cell slurry) | | | Immobilized Enzyme | | |
|---|---|---|---|---|---|---|
| Example | PEI | GA | Chit | Particle Toughness* (%) | Activity IGIU/gm | gm/l |
| 6 | 10.0 | 5.0 | 2.5 | 104 | 438 | 104 |
| 7 | 10.0 | 10.0 | 2.5 | 100 | 421 | 105 |
| 8 | 10.0 | 20.0 | 2.5 | 162 | 403 | 109 |
| 9 | 10.0 | 30.0 | 2.5 | 208 | 270 | 115 |
| 10 | 20.0 | 10.0 | 2.5 | 152 | 409 | 114 |
| 11 | 20.0 | 20.0 | 2.5 | 216 | 367 | 123 |
| 12 | 20.0 | 30.0 | 2.5 | 241 | 336 | 135 |
| 13 | 10.0 | 5.0 | 2.5 | 94 | 690 | 108 |
| 14 | 10.0 | 10.0 | 2.5 | 125 | 502 | 105 |
| 15 | 20.0 | 5.0 | 2.5 | 129 | 705 | 111 |
| 16 | 20.0 | 7.5 | 2.5 | 130 | 650 | 116 |
| 17 | 20.0 | 10.0 | 2.5 | 162 | 592 | 128 |
| 18 | 20.0 | 20.0 | 2.5 | 244 | 436 | 123 |
| 19 | 10.0 | 5.0 | 2.5 | 132 | 458 | 103 |

TABLE 2-continued

| Example | Reagents (g/l of cell slurry) PEI | GA | Chit | Particle Toughness* (%) | Immobilized Enzyme Activity IGIU/gm | gm/l |
|---|---|---|---|---|---|---|
| 20 | 10.0 | 7.5 | 2.5 | 148 | 495 | 105 |
| 21 | 10.0 | 10.0 | 2.5 | 196 | 410 | 104 |
| 22 | 20.0 | 5.0 | 2.5 | 182 | 487 | 102 |
| 23 | 20.0 | 7.5 | 2.5 | 213 | 384 | 114 |
| 24 | 20.0 | 10.0 | 2.5 | 258 | 383 | 117 |

*See Table 1

EXAMPLES 25-30

Immobilizations were carried out in which the chitosan level was varied. The procedure set out in Example I was used using two different levels of PEI and glutaraldehyde. The effect on activity and particle toughness are shown in Table 3. Increasing the level of chitosan improved activity and particle toughness at the two levels of PEI. At the higher level of glutaraldehyde, particle toughess was improved while the activity was not improved at the higher chitosan level. Various levels of chitosan at a third level of PEI were used in the immobilization process (examples 28-30). The results, set out in Table 3, show that above the optimum level of chitosan enzyme recovery is reduced.

TABLE 3

| Example | Reagents (g/l of cell slurry) PEI | GA | Chit. | Particle Toughness* (%) | Immobilized Enzyme Activity (IGIU/gm) | gm/l |
|---|---|---|---|---|---|---|
| 7 | 10.0 | 10.0 | 2.5 | 100 | 421 | 105 |
| 25 | 10.0 | 10.0 | 7.5 | 142 | 492 | 112 |
| 8 | 10.0 | 20.0 | 2.5 | 162 | 403 | 109 |
| 26 | 10.0 | 20.0 | 7.5 | 182 | 389 | 110 |
| 10 | 20.0 | 10.0 | 2.5 | 152 | 409 | 114 |
| 27 | 20.0 | 10.0 | 7.5 | 147 | 480 | 120 |
| 28 | 2.5 | 10.0 | 6.3 | 70 | 529 | 100 |
| 29 | 2.5 | 10.0 | 12.5 | 73 | 576 | 105 |
| 30 | 2.5 | 10.0 | 25.0 | 104 | 425 | 117 |

*See Table 1

EXAMPLES 31-35

PEI samples of various molecular weight were used in the immobilization process described in Example I. The results are set out in Table 4 which shows that the high molecular weight PEI worked best. The immobilization in which the lower molecular weight PEI's were used caused a type of flocculated cell mass that could not be recovered by the usual manner of filtration. It is possible that by altering the levels of the PEI and/or glutaraldehyde and/or chitosan a suitable flocculant could be obtained.

TABLE 4

| Example | PEI Mol Wt. | Reagents g/l cell slurry PEI | GA | Chit. | Particle Toughness** (%) | Immobilized Enzyme Activity (IGIU/gm) | gm/l |
|---|---|---|---|---|---|---|---|
| 31* | Uncertain | 8.1 | 4.0 | 2.0 | 14 | 601 | 88 |
| 32 | P-12 | 8.1 | 4.0 | 2.0 | Could not filter | | |
| 33 | P-18 | 8.1 | 4.0 | 2.0 | Could not filter | | |
| 34 | P-150 | 8.1 | 4.0 | 2.0 | Could not filter | | |
| 35 | P-600 | 8.1 | 4.0 | 2.0 | 67 | 828 | 101 |

*PEI from Kodak as 50% solids
**See Table 1

EXAMPLES 36-40

The order in which glutaraldehyde and chitosan are added in Example I were interchanged. Table 5 demonstrates the activity and particle toughness observed by interchanging the order of addition of glutaraldehyde and chitosan at various levels of PEI. Greater immobilized enzyme activity was obtained when glutaraldehyde was added last although particle toughness was somewhat reduced.

TABLE 5

| Example | Reagents g/l cell slurry 1 | 2 | 3 | Particle Toughness* (%) | Immobilized Enzyme Activity (IGIU/gm) | gm/l |
|---|---|---|---|---|---|---|
| 36 | PEI 10.0 | GA 7.5 | Chit 2.5 | 143 | 670 | 119 |
| 37 | PEI 10.0 | Chit 2.5 | GA 7.5 | 157 | 639 | 128 |
| 38 | PEI 15.0 | GA 7.5 | Chit 2.5 | 185 | 587 | 125 |
| 39 | PEI 15.0 | Chit 2.5 | GA 7.5 | 163 | 638 | 134 |
| 24 | PEI 20.0 | GA 10.0 | Chit 2.5 | 258 | 383 | 117 |
| 40 | PEI 20.0 | Chit 2.5 | GA 10.0 | 216 | 652 | 113 |

*See Table 1

EXAMPLE 41

Heat treated cell slurry, prepared as described in Example 1, was diluted with two volumes of water. To the cell slurry was added 15 grams of PEI, 2.5 grams of chitosan and 7.5 grams of glutaraldehyde per liter of undiluted cell slurry using the procedure of Example 1. The cell mass was collected and dewatered to about 75% moisture in a 12 inch basket centrifuge. Fermentations are run under as identical conditions as possible but cells isolated from various fermentations are not completely identical as far as the texture of the immobilized mass is concerned. Therefore, depending on the batch, the preferred moisture level for forming the spherical particles will vary somewhat between 71 and 75% moisture. The cell cake was extruded through a 1.0 mm die onto the revolving plate of a spheronizing machine comprising a milled friction plate as rotor situated in a cylinder such that the cylinder provides a stationary wall for the plate while allowing it freedom to rotate. The milled plate had a diameter of 23 cm and was milled in the configuration of 2 mm pitch and 1 mm in height. The plate was rotated at a speed of 600 RPM to provide a tangential velocity of 7.2 meters per second for a period of about 2 minutes whereupon the spheronized extrudate was discharged from the machine through an apature by centrifugal force. The spheronized particles were then dried in a fluid bed dryer (Aeromatic AG, Model No. 1) with inlet air temperature of about 68° C. This procedure yielded 108 grams of dried material per liter of cell slurry. This preparation of immobilized glucose isomerase was assayed at 437 IGIU per gram of 20/40 mesh particle size and had 442 particle toughess (relative to 100 in Example 1). A 10 gram (30/40 mesh) portion of this immobilized enzyme was hydrated in 40% (w/w) DS (dry solids) glucose at pH 8.0 containing 4.1 mM magnesium and 250 ppm $SO_2$ at 25° C. for one hour. The hydrated enzyme slurry was then placed in a 60° C. water bath for about two hours and then transferred to a 100×1.5 cm glass jacketed column. Prior to adding the enzyme particles to the column, a small plug of glass wool was placed on the bottom plate followed by the addition of 5 ml of 20/40 mesh aluminum particles. The temperature of the column was maintained at 60° C. Glucose feed was then perculated down through the bed at a flow rate to maintain a fructose conversion of 42–44%. Table 6 illustrates the activity with respect to time, and the productivity as grams DS of 42% fructose per gram of enzyme. The activity decay profile indicates that about 58 days were required to reach the half-life. At the half-life, about 5,060 grams of DS (42% fructose) was produced per gram of immobilized enzyme.

TABLE 6

Stability and Productivity of Immobilized *F. arborescens* at 60° C. using 40% DS (w/w) Glucose Containing 4.1 mM $Mg^{2+}$, and 250 ppm $SO_2$ at pH 8.0 at 25° C.
(see Example 41 for more details)

| Time (days) | Relative Activity | Productivity (g DS) (g enz)$^{-1}$ |
|---|---|---|
| .9 | 100 | 104 |
| 4.9 | 93 | 554 |
| 10.0 | 94 | 1126 |
| 14.8 | 86 | 1632 |
| 20.0 | 82 | 2138 |
| 25.0 | 80 | 2617 |
| 30.1 | 75 | 3077 |
| 34.9 | 69 | 3472 |
| 40.0 | 65 | 3871 |
| 44.9 | 62 | 4234 |
| 49.9 | 57 | 4581 |
| 55.0 | 54 | 4905 |
| 59.9 | 47 | 5184 |
| 64.9 | 42 | 5430 |
| 69.9 | 36 | 5646 |
| 74.9 | 30 | 5824 |
| 79.8 | 24 | 5967 |
| 84.9 | 21 | 6092 |
| 87.9 | 18 | 6159 |

EXAMPLE 42

This example demonstrates that extracellular enzyme can be immobilized by this fixation process. Cell broth of F. arborescens was centrifuged in the usual manner. The cell slurry was diluted with DI water to 34% by volume of the culture broth. The diluted cell slurry was homogenized in a Manton-Gaulin homogenizer at 8,000–10,000 psi. The cell material was passed through the homogenizer three times. The degree of solubilizing the enzyme by homogenization is given in the following table.

TABLE 7

| Material | Soluble Activity % of Total |
|---|---|
| Cell slurry | 2 |
| 1st homogenate | 31 |
| 2nd homogenate | 52 |
| 3rd homogenate | 58 |
| Fixation filtrate | 4 |

The cell material homogenized three times was then immobilized in the following manner. 10 liters of homogenized cell slurry was adjusted to pH 8.0 and then incubated at 70° C. for 15 min. and cooled to about 25° C. Cross-linking was carried out by adding 1038 ml of 5% PEI (P-600, Cordova) followed by 3,460 ml of 0.25% chitosan and lastly adding 347 ml of 10% glutaraldehyde. The pH of the cell mixture was then adjusted to 8.0. Upon addition of glutaraldehyde, complete cell aggregation took place as judged by the clear supernatant fluid. The aggregated cell material was collected in a 12 inch basket centrifuge. The cell cake was then extruded and shaped in spherical particles by the process described in Example 41.

The glucose isomerase activity remaining in the filtrate fluid was found to be only 4% of the total activity (Table 7). This result indicates that practically all the soluble activity was immobilized. The results of immobilization are shown in the following table.

TABLE 8

| Ex-ample | g/liter Cell Slurry | | | | Immobilized Enzyme | | |
|---|---|---|---|---|---|---|---|
| | Treatment | PEI | Chit | GA | IGIU/l | g/l | Toughness (%)* |
| 42 | Homogenized | 29.6 | 4.9 | 19.8 | 476 | 139 | 382 |

*See Table 1

EXAMPLE 43

The culture broth of Streptomyces olivaceous containing glucose isomerase was immobilized in the following manner: Culture broth from S. olivaceous fermentation was used for immobilization. The growth of S. olivaceous is mainly composed of mycelium, whereas in the case of F. arborescens the growth is more of the cellular type. Two liters of culture broth were adjusted to pH 9.0 followed by the addition of 20 ml of 10% PEI (P-600, Cordova) which caused a small amount of flocculation to occur. Next, 30 ml of 10% glutaraldehyde was added which did not cause any apparent increase in the flocculation. Then, 1.5 liter of 0.25% chitosan was added causing complete aggregation of the mycelium. The immobilized cell material was collected by filtration and extruded as in Example 1. The table below summarizes the results.

TABLE 9

| Reagent g/liter of Culture Broth | | | | Immobilized Enzyme | | |
|---|---|---|---|---|---|---|
| Example | PEI | GA | Chit | Particle Toughness (%)* | IGIU/g | g/liter |
| 43 | 1.0 | 1.5 | 1.9 | 257 | 260 | 10.0 |

*See Table 1

EXAMPLE 44

Immobilization of Bacillus licheniformis mutant glucose isomerase.

The following illustrates the immobilization process in which the reagents are added in the order of chitosan-glutaraldehyde-PEI. The growth of B. licheniformis is more like F. arborescens; i.e., cellular, not mycelian. To 1 liter of culture broth adjusted to pH 7.0 was added 20 ml of 10% glutaraldehyde. The cell mixture was diluted with 2 volumes of water, and then 25 ml of 5% PEI (Kodak, molecular weight range uncertain) was added, which caused the cells to aggregate. The immobilized cell mass was collected by filtration and further treated as in Example 1. The table below summarizes the immobilization process.

TABLE 10

| Example | Reagent g/liter of Culture Broth | | | Immobilized Enzyme | |
|---|---|---|---|---|---|
| | Chit | GA | PEI | IGIU/g* | g/liter |
| 44 | .06 | 1.0 | 1.25 | 96.7 | 13.4 |

*Assayed at 70° C.

EXAMPLE 45

Immobilization of glucose isomerase from L. licheniformis. This example illustrates the immobilization process of adding the reagents in the order of GA-Chit-PEI. To 1 liter of culture broth that was adjusted to pH 7.5 was added 250 ml of 1% glutaraldehyde while the pH was maintained at 7.5. Then 1 liter of 0.2% chitosan was added to the culture broth, followed by the addition of 38.4 ml of 5% PEI (Kodak, molecular weight range uncertain). The cell aggregate was collected by filtration and further treated as in Example 1. The table below summarizes the fixation process.

TABLE 11

| Example | Reagent g/liter of Culture Broth | | | Immobilized Enzyme | |
|---|---|---|---|---|---|
| | GA | Chit | PEI | IGIU/g* | g/liter |
| 45 | 2.5 | 2.0 | 1.9 | 99 | 15.1 |

*Assayed at 70° C.

EXAMPLE 46

Another example of the immobilization of glucose isomerase produced from B. licheniformis. For this example, 4 liters of B. licheniformis culture broth were adjusted to pH 7.5 and then incubated at 70° C. for 15 min. After cooling to about 25° C., 2 liters of 0.2% chitosan were then added. The pH of the cell mixture was then adjusted to 9.0 prior to adding 100 ml of 10% glutaraldehyde. Then 80 ml of 5% PEI was added. During the addition of glutaraldehyde and PEI the pH of the mixture was maintained at 9.0. The aggregated cell mass was collected by filtration, extruded and dried as in Example 1. The results of the fixation process are given in the following table.

TABLE 12

| Example | Reagents g/liter of Culture Broth | | | Immobilized Enzyme | | |
|---|---|---|---|---|---|---|
| | Chit | GA | PEI | IGIU/g* | gm/liter | Toughness** |
| 46 | 1.0 | 2.5 | 1.0 | 142 | 113 | 500 |

*Assayed at 70° C.
**See Table 1

What is claimed is:

1. A method for preparing an immobilized enzyme preparation containing an immobilized enzyme having biocatalytic activity selected from the group consisting of sucrose mutase and glucose isomerase comprising:
    (a) introducing to an aqueous medium containing said enzyme or a mass of bacterial cells containing said enzyme an aqueous solution of a polyethylenimine (PEI) having a molecular weight of at least about 500 Daltons with a primary amino group content of at least 10 weight percent of the polymer's amino groups;
    (b) adding glutaraldehyde and an aqueous solution of chitosan to the aqueous medium to form a cross-linked reaction product; and
    (c) removing the cross-linked reaction product from the aqueous medium and drying it to provide said immobilized enzyme preparation.
2. The method of claim 1 wherein in step (a) the aqueous medium contains said mass of bacterial cells containing said enzyme.
3. The method of claim 1 wherein the molecular weight of the polyethylenimine is in the range of from 40,000 to 60,000 Daltons.
4. The method of claim 1 wherein the PEI is placed in aqueous solution at a concentration of 1 to 10 weight percent before its introduction to the aqueous medium.
5. The method of claim 1 wherein the amount of PEI is from 2 to 22 weight percent of the immobilized enzyme preparation.
6. The method of claim 1 wherein the amount of chitosan employed is from 0.5 to 22 weight percent of the immobilized enzyme preparation.
7. The method of claim 6 wherein the amount of chitosan is from 3.5 to 10 weight percent of the immobilized enzyme preparation.
8. The method of claim 1 wherein the amount of glutaraldehyde employed is in an amount of from 4 to 26 weight percent of the immobilized enzyme preparation.
9. The method of claim 8 wherein the amount of glutaraldehyde is from 7 to 15 weight percent of the immobilized enzyme preparation.
10. The method of claim 1 wherein the bacteria cells are a strain of F. arborescens capable of producing glucose isomerase.
11. The method of claim 10 wherein the strain is ATCC 4358.
12. An immobilized enzyme preparation prepared by the method of claim 1.
13. A method of preparing an immobilized enzyme preparation containing an immobilized enzyme having biocatalytic activity selected from the group consisting of sucrose mutase and glucose isomerase comprising:
    (a) introducing to an aqueous medium containing a mass of cells producing said enzyme an aqueous solution containing from 1 to 10 weight percent of polyethylenimine (PEI) having a molecular weight in the range of from 40,000 to 60,000 Daltons and a primary amino group content of at least 10 weight percent of the polymer's amino groups in sufficient quantity to provide PEI in an amount of from 2 to 22 weight percent of the immobilized enzyme preparation;
    (b) adding glutaraldehyde in an amount of from 7 to 15 weight percent of the immobilized enzyme preparation and an aqueous solution of chitosan in a quantity sufficient to provide chitosan in an amount of from 3.5 to 10 weight percent of the immobilized enzyme preparation to the aqueous medium to form a cross-linked reaction product; and
    (c) removing the cross-linked reaction product from the aqueous medium and drying it to provide said immobilized enzyme preparation.
14. A method for preparing a spherical immobilized enzyme preparation containing an immobilized enzyme having biocatalytic activity selected from the group consisting of sucrose mutase and glucose isomerase comprising:

(a) introducing to an aqueous medium containing said enzyme or a mass of bacterial cells containing said enzyme an aqueous solution of polyethylenimine (PEI) having a molecular weight of at least about 500 Daltons with a primary amino group content of at least 10 weight percent of the polymer's amino groups;

(b) adding glutaraldehyde in an amount of from 4 to 26% of the immobilized enzyme preparation and an aqueous solution of chitosan in an amount sufficient to provide chitosan in an amount of from 0.5 to 22 weight percent of the immobilized enzyme preparation to form a cross-linked reaction product;

(c) removing the cross-linked reaction product from the aqueous medium and partially drying it to form a wet cake;

(d) extruding the wet cake through an orifice onto the rotating plate of a spheronizing device which comprises a milled friction plate as rotor situated in a cylinder such that the cylinder provides a stationary wall for the plate while allowing it to rotate to form said spherical immobilized enzyme preparation.

15. The method of claim 14 wherein the wet cake contains from 68 to 76 weight percent water.

16. The method of claim 14 wherein the plate is rotating at a speed sufficient to provide a tangential velocity of from 4.5 to 12 meters per second.

17. A method for preparing a spherical immobilized enzyme preparation containing an immobilized enzyme having biocatalytic activity selected from the group consisting of sucrose mutase and glucose isomerase comprising:

(a) introducing to an aqueous medium containing a mass of cells producing said enzyme an aqueous solution containing from 1 to 10 weight percent of polyethylenimine (PEI) having a molecular weight in the range of from 40,000 to 60,000 Daltons and a primary amino group content of at least 10 weight percent of the polymer's amino groups in sufficient quantity to provide PEI in an amount of from 2 to 22 weight percent of the immobilized enzyme preparation;

(b) adding glutaraldehyde in an amount of from 7 to 15 weight percent of the immobilized enzyme preparation and an aqueous solution of chitosan in a quantity sufficient to provide chitosan in an amount of from 3.5 to 10 weight percent of the immobilized enzyme preparation to the aqueous medium to form a cross-linked reaction product;

(c) removing the cross-linked reaction product and partially drying it to form a wet cake containing from about 68 to 76 weight percent water;

(d) extruding the wet cake through an orifice on to the plate of a spheronizing device which comprises a milled friction plate as rotor situated in a cylinder such that the cylinder provides a stationary wall for the plate while allowing it to rotate wherein said plate is rotated at a speed sufficient to provide a tangential velocity of from 4.5 to 12 meters per second during the extrusion step and for a time sufficient to form said spherical immobilized enzyme preparation.

18. The method of claim 17 wherein the cells are those of a strain of F. arborescens capable of producing glucose isomerase.

19. The method of claim 18 wherein the strain is ATCC 4358.

* * * * *